United States Patent [19]
Kiyonaga et al.

[11] Patent Number: 5,356,600
[45] Date of Patent: Oct. 18, 1994

[54] OXYGEN ENRICHMENT METHOD AND SYSTEM

[75] Inventors: Kazuo Kiyonaga, Honolulu, Hi.; Lawrence M. Litz, Pleasantville; Thomas J. Bergman, North Tarrytown, both of N.Y.

[73] Assignee: Praxair Technology, Inc., Danbury, Conn.

[21] Appl. No.: 586,945

[22] Filed: Sep. 24, 1990

[51] Int. Cl.$^5$ .............. B01F 1/00; B01J 8/00; C12M 1/04; C12M 1/06
[52] U.S. Cl. ............... 422/234; 422/231; 435/313; 435/315; 435/818; 435/243; 261/36.1; 261/16; 261/93; 261/DIG. 75
[58] Field of Search .......... 435/315, 314, 313, 309, 435/818, 243; 422/231, 225, 234; 261/93, 16, 36.1, DIG. 75

[56] References Cited

U.S. PATENT DOCUMENTS

| | | | |
|---|---|---|---|
| 3,054,814 | 9/1962 | Jason et al. | 260/413 |
| 4,001,090 | 1/1977 | Kalina | 195/109 |
| 4,036,699 | 7/1977 | Quigg | 435/818 |
| 4,670,397 | 6/1987 | Wegner et al. | 435/243 |
| 4,782,024 | 11/1988 | Scott et al. | 435/818 |
| 4,867,918 | 9/1989 | Kiyonaga et al. | 261/76 |
| 4,900,480 | 2/1990 | Litz et al. | 261/93 |

FOREIGN PATENT DOCUMENTS 3632570 4/1988 Fed. Rep. of Germany ...... 435/818

Primary Examiner—Michael G. Wityshyn
Assistant Examiner—T. J. Reardon
Attorney, Agent, or Firm—Alvin H. Fritschler

[57] ABSTRACT

In systems in which air is introduced into a liquid as a source of oxygen, additional oxygen added independent of the feed air enhances the oxygen content of the liquid source significantly than if the same amount of additional oxygen were combined with the feed air.

5 Claims, 2 Drawing Sheets

OXYGEN ENRICHMENT METHOD AND SYSTEM

BACKGROUND OF THE INVENTION

1. Field of the Invention

The invention relates to the dissolution and/or reaction of oxygen in liquids. More particularly, it relates to the enhancing of the rate of said dissolution and/or reaction.

2. Description of the Prior Art

Air is commonly used as a source of oxygen in liquid phase systems to increase the dissolved oxygen concentration and/or to introduce oxygen as a reactant material. In some circumstances, it is desired to dissolve more oxygen to the liquid phase than an air-fed system can supply. The quantity of oxygen capable of being dissolved in the liquid phase from the air feed may be limited because of the inadequate mass transfer capabilities of a specific system. Also, the available air blower capacity may be inadequate to supply more air, or the system may not be able to tolerate a higher vent gas flow or, perhaps, a higher oxygen content in the vent stream.

A typical means used to improve the oxygen input rate is to increase the mass transfer rate by enriching the oxygen content of the air feed stream with pure oxygen or an oxygen-rich gas. Because the mass transfer efficiencies of commercial operating systems are often not particularly good, however, a large fraction of the added oxygen is typically lost in the vent stream. Such losses substantially increase the cost of using oxygen in this manner. In some cases, the additional oxygen cost can make such enrichment uneconomical. In addition, excessive loss of added oxygen into the vent stream increases the oxygen content of said vent stream, so that the composition of the vent gases could get into the explosive range with organic oxidation systems.

There is a desire and a need in the art to overcome such drawbacks in practical commercial gas dissolution and/or reaction operations. In particular, there is a need to improve oxygen utilization efficiency, the rate of oxygen dissolution and/or reaction and, to the extent possible, product yield in chemical reactions and/or gas dissolution systems involving oxygen where the use of additional oxygen is desired above that supplied by a feed air stream.

It is an object of the invention, therefore, to provide an improved process for the dissolution and/or reaction of oxygen in liquid systems.

It is another object of the invention to provide for increasing the efficiency of oxygen utilization in air/liquid dissolution and/or reaction systems.

It is a further object of the invention to provide a process for reducing the loss of added oxygen with the vent stream as occurs in applications in which oxygen or an oxygen-rich gas is added to an air feed stream to increase the oxygen input rate in oxygen dissolution and/or reaction systems.

With these and other objects in mind, the invention is hereinafter described in detail, the novel features thereof being particularly pointed out in the appended claims.

SUMMARY OF THE INVENTION

In systems wherein air is being introduced into a liquid as a source of oxygen, additional oxygen is added as a gas, or as an oxygen-rich liquid, independent of the air stream, with the resulting oxygen content of the liquid being significantly higher than if the same amount of additional oxygen was combined with the feed air stream.

BRIEF DESCRIPTION OF THE DRAWINGS

The invention is hereinafter further described with reference to the accompanying drawings in which.

DETAILED DESCRIPTION OF THE INVENTION

Figure 1:
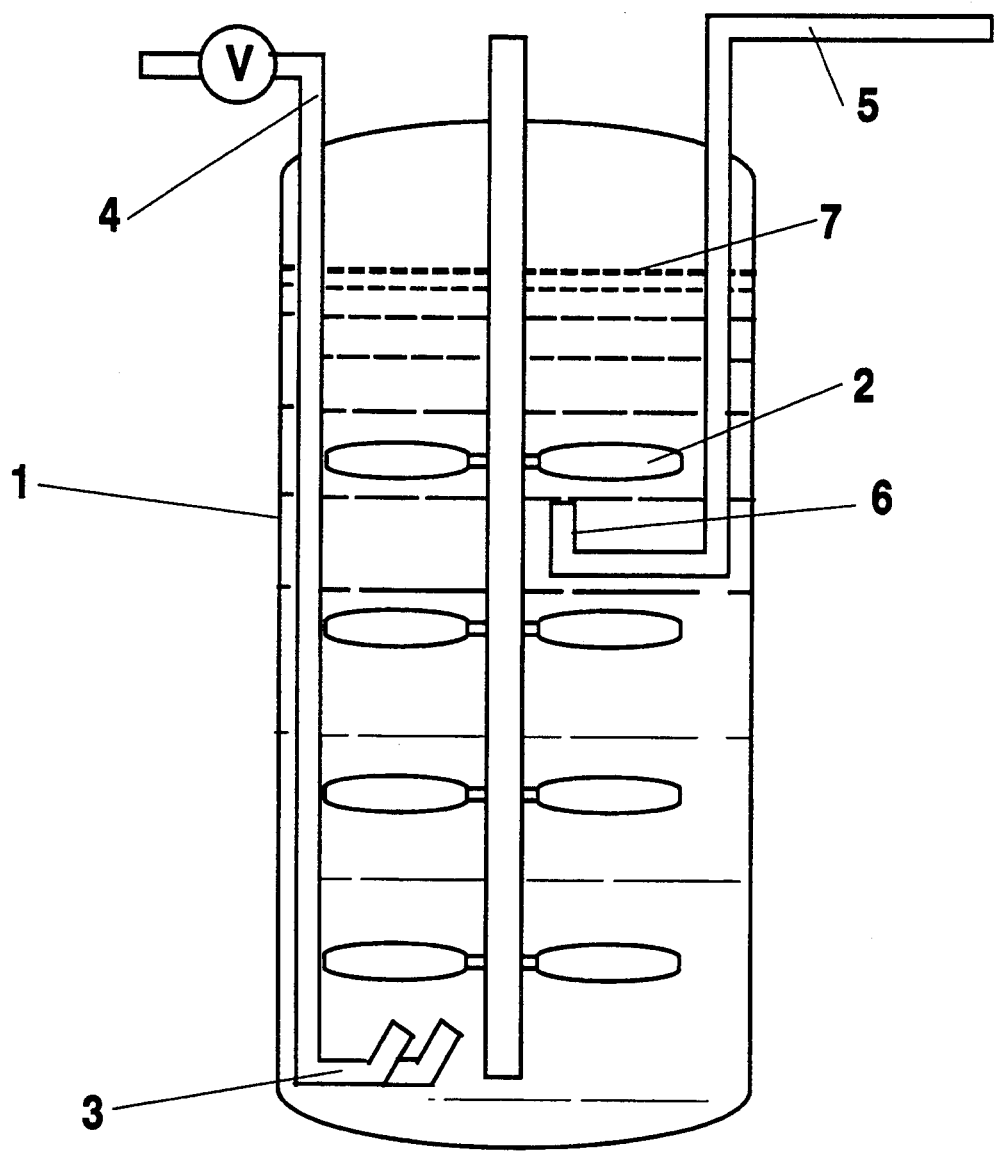
FIG. 1 is a side elevational view of an air-fed fermenter system adapted for the practice of the invention.

The objects of the invention have been accomplished by the discovery that the introduction of supplemental oxygen into the liquid phase separate from a feed air stream enables oxygen utilization efficiency to be increased in air/liquid dissolution and reaction systems. Thus, the oxygen content of the liquid is significantly higher when separate oxygen is added, either as a pure gas, an oxygen-enriched gas or an oxygen-rich liquid, independently of feed air stream, as compared with the addition of the same amount of oxygen combined with the air stream.

In the practice of the invention, it is desirable that the oxygen-rich feed stream be separated from the air feed stream insofar as practical in particular commercial gas/liquid dissolution and/or reactor systems. When gaseous oxygen is used, the location of the oxygen injection point, and the trajectory of the bubble stream issuing from the oxygen injector should be chosen so that the mixing and/or coalescence of the oxygen bubbles with feed air bubbles is minimized. Similarly, when an oxygen-rich feed stream, as from a side-stream pumping system, is introduced into an aerated tank, the injection point should be located to the extent possible at a position remote from the air injection point.

By the practice of the invention, higher dissolved oxygen concentrations and higher oxygen utilization efficiencies can be obtained than in conventional practice. When gaseous oxygen is employed, this is apparently because gas bubbles containing significantly higher oxygen concentrations than in air bubbles can coexist with said air bubbles. Also, because of the typically lower oxygen gas volumes compared to the volume of air being fed to the system and because of the injection techniques desirably used in the practice of the invention, the oxygen-rich bubbles may be smaller than the air bubbles. Both of these factors, higher oxygen concentration and smaller bubble size, can substantially increase the rate of transfer of oxygen from the oxygen-rich bubbles to the liquid as compared with such transfer from air bubbles.

When an oxygen-rich liquid is employed in the practice of the invention, the advantages referred to above accrue because the injected air bubbles are not very effective in stripping oxygen from the oxygen-rich liquid. This was observed in tests carried out in an approximately 400 gallon tank of water, into which air was sparged through a conventional perforated pipe-ring sparger placed at the bottom of the tank. A mechanical mixer was used to assure that the water in the tank was well stirred, and a commercial dissolved oxygen analyzer was used to determine the oxygen concentration in the water.

An external recirculating loop was employed for the recirculation of water, and varying amounts of oxygen were added thereto to provide a source of both oxygen gas and of water with a high dissolved oxygen content to the tank. Typically, about 40% to about 60% of the oxygen gas fed into the loop became dissolved in the loop prior to being injected into the aerated tank. The remaining gas issued as fine gas bubbles from an orifice located at the terminus of the loop in the tank. The orifice was positioned such that the stream exiting therefrom did not intercept the column of bubbles rising up from the air sparger.

Using such test equipment, the dissolved oxygen level was determined in the water tank into which air was injected, while pure oxygen was passed into the side-stream recirculating loop. The total volume of liquid in the tank was 305 gals, the liquid pumping rate was 5 gpm, and the water temperature was 15° C. The oxygen feed to the loop was incrementally increased from 0 up to 1.3 scfm. When no oxygen was being fed, the saturated oxygen concentration in equilibrium with the air was about 10.2 parts per million (ppm=mg/l). In this set of experiments, the addition of 1.3 scfm of oxygen to the loop, at a 22 scfm air flow rate, resulted in an equilibrium dissolved oxygen concentration of about 17 ppm. This represented a 67% higher dissolved oxygen concentration than that obtained with air alone. If this amount of oxygen gas was mixed with the incoming air, the saturation dissolved oxygen concentration would increase only about 21.2%. It will be appreciated that the practice of the invention not only enables a much higher dissolved oxygen concentration to be achieved, but enables the fraction of the added oxygen lost with the escaping gas to be very sizably reduced. The experiments also established that, when the amount of air being sparged into the tank is increased at a given added oxygen rate, more of the oxygen is carried out by the air, thus lowering the final dissolved oxygen concentration. However, even at an air rate of 41 scfm, the resultant dissolved oxygen concentration was still increased by more than 30% over that obtained by the use of air alone.

With reference to FIG. 1 of the drawings, a large, commercial scale, air-fed fermenter vessel represented by the numeral 1 has therein a set of four down-pumping impellers 2. Air is sparged into vessel 1 through air sparger 3 positioned below the lowest impeller with air from an external source being passed to air sparger 3 through air line 4. Using air injection alone, this system, as with many such commercial fermentation systems, was unable to supply enough oxygen from the air feed to sustain the desired growth rate during the multi-day fermentation cycle, when the microorganism growth rate was at its maximum.

Oxygen gas was separately fed into the system through line 5 from an independent source of oxygen (not shown). Because the normal flow pattern within the zone of impellers 2 was downward, a preferred position for oxygen injection nozzle 6 was below the uppermost impeller. From this location, most of the oxygen bubbles formed at the injection point would be carried into the next lower impeller by the down-flowing liquid in impeller zone 2. As a result, the oxygen gas bubbles would be dispersed and well mixed into the liquid stream.

The liquid flow pattern would continue to bring the undissolved oxygen bubbles down through the high turbulence zone of the successively lower impellers to further enhance the desired dissolution of said oxygen in the liquid. It should be noted that oxygen injection nozzle 6 is not preferably located above the uppermost impeller 2 and in the vicinity of fermentation liquid level 7 because some air is usually ingested at that point, and this would tend to dilute the pure oxygen being separately injected into vessel 1.

It should be noted that any appropriate means for injecting the oxygen stream into the system can be employed in the practice of the invention. Thus, a simple pipe injector can be employed. To improve gas dispersion, the exiting oxygen gas velocity can be increased to improve the oxygen bubble dispersion by using a pipe with a restrictive orifice, or with multiple orifices, at the nozzle end thereof. In addition, the orifice(s) and the oxygen supply pressure can be selected to feed the gas into the liquid at supersonic velocities, as is known in the art to produce enhanced dispersion of the gas in the liquid.

In experiments using a fermenter as shown in FIG. 1, the oxygen dissolution efficiency, based on the use of feed air alone, was on the order of 15%. When additional oxygen was injected into vessel 1 through injection nozzle 6, tile dissolution efficiency for the added oxygen was about 30% under the same operating conditions.

While the additional oxygen was being supplied to the system in the practice of the invention, the system could be run under much high organism growth rate conditions, while still maintaining the dissolved oxygen level at least at 30% of air saturation. If only air were to be fed to the system under such high growth rate conditions, the dissolved oxygen level would fall close to zero, even at the maximum air flow available. As a consequence of being able to supply more oxygen to the system, an increase as high as about 43% in the production rate of the fermenter was obtained. It will be understood that the use of some air is necessary to strip carbon dioxide from the fermenter liquid.

Figure 2:
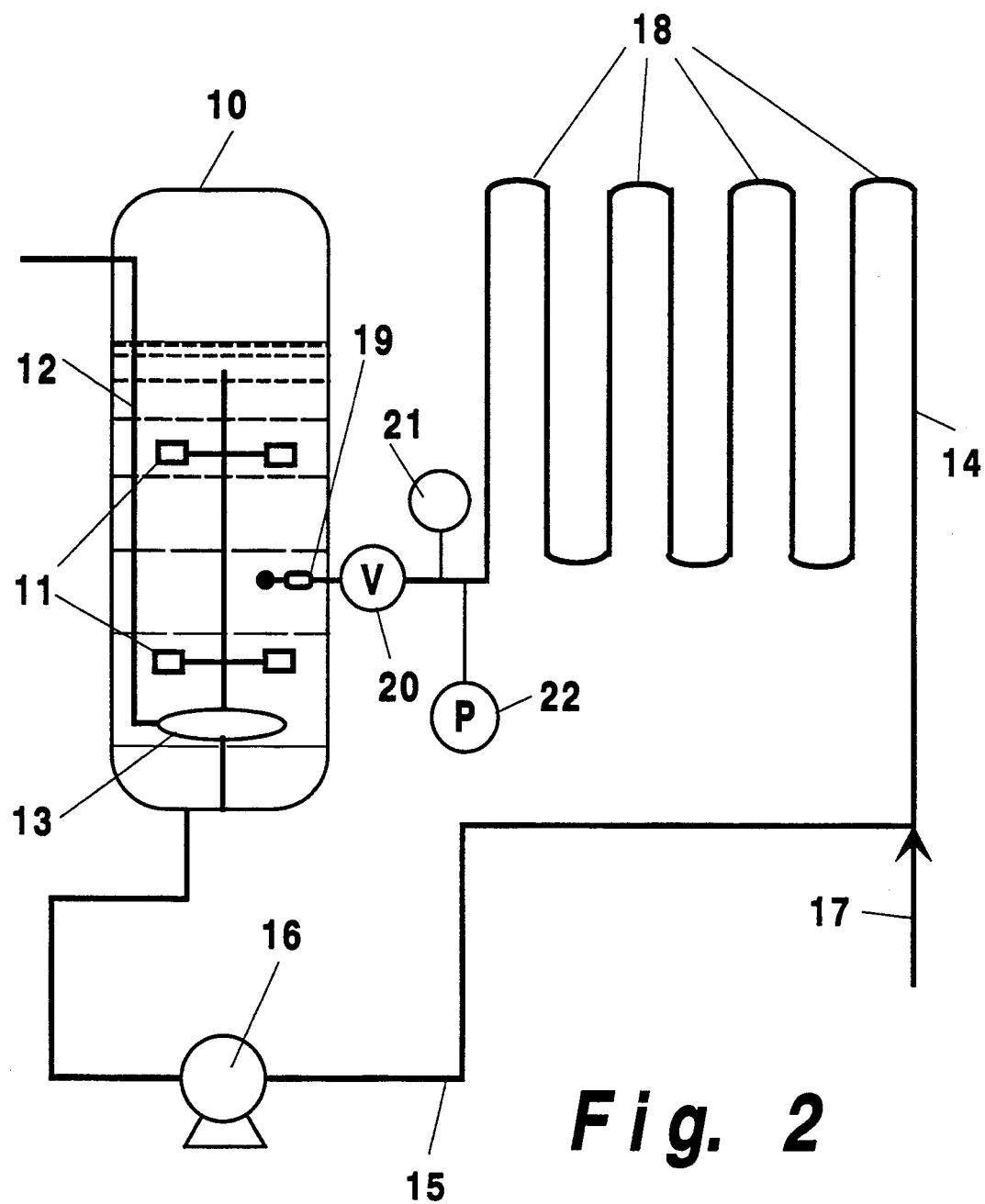
FIG. 2 is a schematic drawing of an embodiment of the invention comprising an air-fed fermenter, including a pipe-loop gas contacting system to augment the oxygen supplied to said fermenter.

FIG. 2 of the drawings illustrates a pilot scale fermenter in which it was also demonstrated that the dissolved oxygen concentration is increased, and the operation of the fermenter enhanced, by the use of the method and system of the invention. In this embodiment, a 500 liter fermentation tank 10 contains therein a pair of standard Rushton radial flow turbines 11 for mixing purposes, with air feed through line 12 being to air sparger 13 positioned below the lowest turbine 11. A pipe-loop gas contacting system 14, i.e. a side-stream pumping system, was employed to augment the oxygen supplied by the air feed with pure oxygen. In this supplemental system, liquid is pumped from tank 10 through line 15 by pump 16, and pure oxygen is injected into the line from oxygen supply line 17. The gas/liquid mixture formed thereby passes in said line 15 through gas dissolver loop section 18 and passes to loop injector 19 positioned so as to inject the gas/liquid stream into fermenter tank 10, preferably at a point, as illustrated, between the two turbines 11. Appropriate valve means, such as the illustrated valve 20, can be used to control the recirculation rate, and dissolved oxygen and pressure measurement means 21 and 22 can be provided for further monitoring and control of the overall operation.

In the practice of this embodiment of the invention, liquid from fermenter tank 10 was recirculated at a rate of 500 to 1,000 liters per hour by pump 16, which also elevated the pressure from near atmospheric to about 60 to 100 psig. Oxygen was fed into loop 14 through line 17 at flow rates up to about 6 liters (stp) per minute. In operation, about 30 to 60% of this oxygen was dissolved in the fermentation liquid, while the remainder was discharged into tank 10 as a gas. This liquid/gas mixture was reintroduced into tank 10 between upper and lower impellers 11. Employing loop injector 19 at the discharge end of loop 14 removed from the vicinity of air sparger 13, in the form of a venturi-type injector, contributed to a two to three-fold increase in oxygen use efficiencies as well as oxygen dissolution rates. The increased oxygen concentration in the fermenter resulted in a significant rise in the respiration rate of the organisms in the fermentation broth.

In various embodiments of the invention, it may be feasible to circulate some of the process fluid through an injector, with or without dissolver loop section 18 referred to above, with said injector desirably being in the form of a gas/liquid dispersion device to provide an extremely fine dispersion of the incoming oxygen in the liquid. Since the rate of gas dissolution is proportional to the surface area of the gas-liquid interface surrounding the gas bubbles, the dissolution rate is increased as the bubble dispersion is made finer. Typically, this will translate into improved oxygen utilization efficiency. One advantageous gas dispersion device, which was the subject of the Kiyonaga et al patent U.S. Pat. No. 4,867,918, provides for the combining of the gas and liquid in close proximity to a venturi or other flow constriction means used to create supersonic flow velocities and subsequent deacceleration to subsonic velocity. When a venturi-type injector is employed in such device, the gas-liquid mixing is carried out in the converging portion of the venturi or upstream but in close proximity to the venturi, and the gas-liquid mixture is accelerated to a velocity in excess of the speed of sound in said mixture in said converging section of venturi, or by the presence of orifice means or other flow constriction means in the line.

The invention can be practiced in a variety of applications, such as in a chemical reactor used to carry out oxidations of organic chemicals, such as the oxidation of cumene to cumene hydroperoxide, the precursor to phenol. In such applications, air is typically fed into a piping manifold system from which it is injected into the liquid phase through a multitude of holes. A consequence of this mode of air injection is that the air bubbles rise as a series of parallel curtains. By separately injecting the oxygen at locations between the rising curtains of air, the oxygen-rich bubbles will flow between the curtains of air bubbles, thereby avoiding significant coalescence of the oxygen with the air bubbles. A gas dispersion device, such as referred to above, is an appropriate device for use in cumene oxidation systems and other such systems in which it is common practice to remove the heat of reaction by circulating the reactor charge through an external heat exchanger.

It will thus be appreciated that the rate of solution of oxygen, as well as the oxygen utilization efficiency, will be higher by the separate addition of oxygen at a point removed from the point of injection of feed air in accordance with the invention than if an equivalent amount of oxygen were used to enrich the air feed stream. Also, by locating the injection nozzles at a moderate distance above the bottom of the reactor, the oxygen concentration in the liquid can be advantageously increased in the upper zones of the reactor.

The oxygen content of the original air bubbles is substantially depleted as they rise up through the reactor volume. Consequently, the mass transfer rate of oxygen from these gas bubbles is proportionately reduced. To stay below the explosive range in such reactors, the system is normally operated so that the exiting air bubbles contain no more than about 4 to 6% oxygen, compared with the approximately 21% oxygen content of the air feed. At this low oxygen concentration, the dissolution driving force is rather low. Therefore, the oxygen mass transfer rate in the upper part of the reactor will be much lower than in the bottom region where the feed air is introduced, a circumstance obviated in the practice of the invention.

Those skilled in the art will appreciate that various changes can be made in the details of the method and system described herein without departing from the scope of the invention as set forth in the appended claims. As an illustrative example of the type of change that may be made in practice, a series of tests was carried out in a commercial fermenter employing a somewhat different impeller arrangement than described above. Rather than downpumping impellers, the mixing of the liquid and gas in the fermenter was accomplished using an impeller unit comprising a set of four axial flow impellers, commonly referred to as Rushton turbines, aligned one above the other on the mixer shaft. Air was fed into the fermenter below the lowest impeller.

During the period of maximum oxygen demand by the organisms in the fermenter, the dissolved oxygen level would drop to as low as 10–15% of the air saturation value. This was believed to be an undesirably low condition. However, it was not possible to increase the oxygen concentration appreciably above this level, even using the maximum amount of air that could be fed to the system through the air sparger positioned at the bottom of the fermenter. In accordance with the practice of the invention, an oxygen injection tube with a gas dispersing nozzle on the end was installed in the fermenter. With radial flow impellers, the liquid flow pattern tends to carry the air feed bubbles toward the wall of the fermenter tank. Therefore, to minimize the mixing of the oxygen bubbles with the air bubbles, while still providing a large liquid height above the point of oxygen injection, the oxygen injector was placed so that the oxygen bubble stream would flow underneath the second lowest impeller from the bottom. The liquid flow of said second lowest impeller would then carry the oxygen bubbles out through its blades, resulting in a fine oxygen bubble dispersion in a zone of lower air bubble concentration. This will be seen to involve a particular embodiment of the invention wherein the separate oxygen injection is made at a point remote from the vicinity of the point at which air is passed to a gas-liquid mixing vessel, e.g. the fermenter, and at a convenient location for the purposes of the operation.

In a typical run using this fermenter system, air only was fed until the oxygen demand of the growing microorganisms resulted in the dissolved oxygen level dropping from the initial 75% of air saturation to about 60%. At this rate, pure oxygen feed was initiated through the injector at a rate equal to about 20% of the oxygen present in the incoming air feed stream. Within about ten minutes, the dissolved oxygen level had risen to about 75% of air saturation.

Even at the time of maximum oxygen demand, the dissolved oxygen level did not drop below 30% when the additional oxygen was fed in addition to the air feed. During one of the runs, the oxygen feed was turned off and then on again while maintaining the air feed at its normal rate. The dissolved oxygen concentration increased upon introducing pure oxygen and decreased during periods in which pure oxygen was not supplied. After about 55 hours into the run, the oxygen demand began to fall off so that the air feed alone was able to bring about an increase in the dissolved oxygen concentration.

It was determined that while only 20% more oxygen was being supplied from the pure oxygen supply, 49.4% of the total oxygen dissolved came from this source. This illustrates the much greater dissolution rates resulting from the much higher oxygen partial pressure in the oxygen bubbles introduced separately in accordance with the invention as compared with the introduction of oxygen in the air feed to the system. In these tests, over 35% of the added pure oxygen went into solution. If the same amount of oxygen had been admixed with the air feed stream for enrichment purposes, only about 12% of such oxygen would have been dissolved in the liquid, the air stream having had its oxygen concentration increased from normal 21% to about 25%.

The rate of oxygen dissolution can be expressed as $dc/dt = k_1a(C_s - c)$, where $dc/dt$ is the dissolution rate, $k_1a$ is the mass transfer coefficient, $C_s$ is the saturation concentration of oxygen, and $c$ is the actual dissolved oxygen concentration. The difference between $C_s$ and $c$ is the driving force for dissolution of the oxygen gas in the liquid. Since $C_s$ is directly proportional to the oxygen partial pressure in the gas bubble, which is about 5 times higher for pure oxygen than for air, it will be appreciated that the rate of solution will be much higher for the liquid in contact with oxygen bubbles than for air bubbles or bubbles of moderately enriched air.

Those skilled in the art will appreciate that the amount of oxygen employed in any particular application, relative to the amount of oxygen added in the air or oxygen-enriched air feed, will vary depending on the particular features of the application, such as the particular liquid involved, the purpose of the particular dissolution or reaction operation, the operating conditions pertaining to the application, the features of the mixing system employed and the like. Thus, the amount of supplemental oxygen added may be less than the amount of oxygen added from the feed air stream, or said supplemental oxygen may be employed in an amount greater than the oxygen supplied by said feed air.

It will be understood that the supplemental oxygen can be added as pure oxygen, oxygen-rich gases, and/or liquids containing high dissolved oxygen concentrations, to aerated liquid systems. The practice of the invention, which involves the placement of the supplemental oxygen, or the fluid injection device for said supplemental oxygen injection, such that the issuing stream substantially does not mix with the air bubbles injected into the liquid, results in higher dissolved oxygen content liquids and higher oxygen utilization efficiency, than would have been obtained if the additional oxygen had been added to the aeration air stream. As noted above, the invention enables enhanced dissolved oxygen concentrations to be obtained in fermentation systems, as well as enhanced organic oxidation processes. In addition, the invention facilitates enhancement of municipal and industrial waste treatment operations, and improvement in systems requiring an increase in dissolved oxygen levels, such as in high biological oxygen demand (BOD) effluent streams, water for fish farms and the like. The overall benefits of the invention are achieved using, for gas injection, supersonic gas injection nozzles, simple pipes or gas spargers, orifices, venturi type nozzles or gas-liquid nozzles, depending on the requirements of a given application. If a high oxygen content liquid, or liquid plus oxygen gas is used in the practice of the invention, the injection device for supplemental oxygen addition may be simple pipes, spargers, venturi nozzles or gas-liquid nozzles as desired for the particular application. In all such embodiments the injection of supplemental oxygen gas, or of oxygen-rich liquid, is arranged so that minimal mixing of the oxygen rich stream with the air bubbles occurs and the mixing and/or coalescence of the oxygen bubbles with feed in bubbles is minimized. The invention, as so practiced, provides a highly desirable advance in the art, enabling desirably higher dissolved oxygen concentrations, and high oxygen utilization efficiencies to be obtained than have heretofor been obtainable in the conventional practice pertaining to practical, commercially significant air/liquid dissolution and/or reactor systems.

We claim:

1. A method for enhancing the dissolution and/or reaction of oxygen in liquids comprising:
   (a) maintaining a body of liquid in a mixing vessel;
   (b) injecting a feed air stream into said body of liquid from an air injection point as air bubbles for dissolution and/or reaction of oxygen therein in said liquid;
   (c) passing a portion of the liquid in the mixing vessel through a gas-liquid nozzle;
   (d) passing oxygen or an oxygen-rich gas through said gas-liquid nozzle to provide a fine dispersion of oxygen bubbles in said portion of the liquid passed through the gas-liquid nozzle;
   (e) separately injecting the fine dispersion of oxygen bubbles in said portion of liquid passed through the gas-liquid nozzle into the mixing vessel from an oxygen injection point positioned apart from the air injection point so as to minimize mixing of additional oxygen bubbles with the coexisting air bubbles injected from said air injection point;
whereby the oxygen content of the liquid is enhanced over that obtained if the same amount of oxygen were combined with the feed air stream being injected into said body of liquid, thereby enhancing the dissolved oxygen concentration in the liquid and/or the oxygen utilization efficiency of the dissolution and/or reaction operation.

2. The method of claim 1 in which the gas passed through the gas-liquid nozzle comprises oxygen.

3. The method of claim 1 in which the portion of the liquid in the mixing vessel that is passed through the gas-liquid nozzle is passed through an external side-stream recirculation loop, said gas-liquid nozzle being positioned at the discharge end of said recirculation loop, the oxygen or oxygen-rich gas being injected into the liquid in said recirculation loop for passage through said gas-liquid nozzle.

4. A system for enhancing the dissolution and/or reaction of oxygen in liquids comprising:
   (a) a mixing vessel containing a body of liquid therein;

(b) feed air injection means for injecting a feed air stream as air bubbles into said body of liquid from an air injection point for dissolution and/or reaction of oxygen therein in said liquid;

(c) an external side-stream recirculation loop for said liquid in the mixing vessel;

(d) oxygen injection means for injecting oxygen or an oxygen-rich gas into the liquid in the recirculation loop as additional oxygen bubbles in an oxygen-rich liquid stream;

(e) a venturi injector positioned at the discharge end of the recirculation loop for injecting the oxygen-rich liquid stream from the recirculation loop back into the mixing vessel, said discharge end of the recirculation loop being positioned apart from the vicinity of the air injection point so as to minimize mixing of oxygen from said oxygen-rich liquid stream with the coexisting air bubbles from said air injection point, whereby the oxygen content of the liquid is enhanced over that obtained if the same amount of oxygen were combined with the feed air stream being injected into the body of liquid, thereby enhancing the dissolved oxygen concentration in the liquid and/or the oxygen utilization efficiency of the dissolution and/or reaction operation.

5. A system for enhancing the dissolution and/or reaction of oxygen in liquids comprising:

(a) a mixing vessel containing a body of liquid therein;

(b) feed air injection means for injecting a feed air stream as air bubbles into said body of liquid from an air injection point for dissolution and/or reaction of oxygen therein in said liquid;

(c) oxygen injection means for injecting additional oxygen, independent of said feed air stream, into said body of liquid from an oxygen injection point positioned apart from the vicinity of the air injection point so as to minimize mixing of additional oxygen bubbles with the coexisting air bubbles from said air injection point, said oxygen injection means comprising a gas-liquid injection nozzle for injecting a gas-liquid mixture into the mixing vessel;

(d) means for passing a portion of the liquid from the mixing vessel through said injection nozzle; and (e) means for passing oxygen or an oxygen-rich gas through said injection nozzle to provide a fine dispersion of oxygen bubbles in the gas-liquid mixture injected into the mixing vessel, whereby the oxygen content of the liquid is enhanced over that obtained if the same amount of liquid were combined with the feed air stream being injected into said body of liquid, thereby enhancing the dissolved oxygen concentration in the liquid and/or the oxygen utilization efficiency of the dissolution and/or reaction operation.

* * * * *